United States Patent
Lagrange et al.

(10) Patent No.: US 7,670,390 B2
(45) Date of Patent: Mar. 2, 2010

(54) USE OF LATENT PIGMENTS FOR HIGH-REMANENCE DYEING, COMPOSITION CONTAINING THE SAID PIGMENTS AND PROCESSES USING THEM

(75) Inventors: Alain Lagrange, Coupvray (FR);
Sylvain Kravtchenko, Asnieres (FR);
Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/013,800

(22) Filed: Jan. 14, 2008

(65) Prior Publication Data

US 2008/0172806 A1    Jul. 24, 2008

Related U.S. Application Data

(62) Division of application No. 10/715,839, filed on Nov. 19, 2003, now Pat. No. 7,326,255.

(60) Provisional application No. 60/502,655, filed on Sep. 15, 2003.

(30) Foreign Application Priority Data

Nov. 20, 2002   (FR) .................................. 02 14535

(51) Int. Cl.
*A61Q 5/10*   (2006.01)
(52) U.S. Cl. ................. 8/405; 8/428; 8/429; 8/431; 8/435; 8/437; 8/454; 132/202; 132/208
(58) Field of Classification Search ............... 8/405, 8/428, 429, 431, 435, 437, 454; 132/202, 132/208
See application file for complete search history.

(56) References Cited

U.S. PATENT DOCUMENTS

| | | | |
|---|---|---|---|
| 2,528,378 A | 10/1950 | Mannheimer et al. | |
| 2,781,354 A | 2/1957 | Mannheimer et al. | |
| 6,160,037 A * | 12/2000 | Leugs et al. | ................ 523/205 |
| 7,326,255 B2 * | 2/2008 | Lagrange et al. | ................ 8/405 |

FOREIGN PATENT DOCUMENTS

| | | |
|---|---|---|
| EP | 0 892 018 | 1/1999 |
| WO | WO 98/32802 | 7/1998 |

OTHER PUBLICATIONS

French Search Report for FR 02 14535 (Priority Application for U.S. Appl. No. 10/715,839), dated Nov. 3, 2003.
M.R. Porter, "Handbook of Surfactants", published by Blackie & Son (Glasgow and London), 1991, pp. 116-178.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The invention relates to the use, for dyeing keratin fibers, of at least one latent pigment, which is soluble in a medium that is suitable for dyeing, and which can be chemically, thermally or photochemically converted in the fibers into water-insoluble pigments, of formula $$A(B)_x$$

with A representing the chromophoric radical of dyes,
and B representing a hydrogen atom or a group of formula (II)

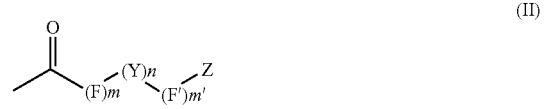

with Z representing a cationic water-solubilizing group $Z^+$ or a polyethylene glycol residue, Y representing a hetero atom, F and F' representing a linear or branched $C_1$-$C_{14}$ alkylene chain, which may contain hetero atoms and may be substituted with one or more hydroxyl, amino or halogen groups. The invention also relates to processes for dyeing keratin fibers using latent pigments, to particular compositions containing them and to multi-compartment dyeing devices or "kits".

33 Claims, No Drawings

USE OF LATENT PIGMENTS FOR HIGH-REMANENCE DYEING, COMPOSITION CONTAINING THE SAID PIGMENTS AND PROCESSES USING THEM

This is a Divisional Application of application Ser. No. 10/715,839, filed Nov. 19, 2003, now U.S. Pat. No. 7,326,255 B2, which claims the benefit of Provisional Patent Application No. 60/502,655, filed Sep. 15, 2003, and which claims the benefit of French Patent Application No. 02 14535, filed Nov. 20, 2002, all of which are incorporated herein by reference.

The invention relates to the use of latent pigments for dyeing keratin fibres, preferably human keratin fibres and in particular the hair, to processes for dyeing human keratin fibres using these compounds and to particular compositions containing these compounds.

It is known practice to dye human keratin fibres, and in particular the hair, with dye compositions containing oxidation dye precursors, which are generally known as oxidation bases. These oxidation bases are colourless or weakly coloured compounds, which, when combined with oxidizing products, give rise to coloured compounds by a process of oxidative condensation.

It is also known that the shades obtained with these oxidation bases may be varied by combining them with couplers or coloration modifiers. The variety of molecules used as oxidation bases and couplers allows a wide range of colours to be obtained.

This oxidation dyeing process consists in applying to the keratin fibres oxidation bases or a mixture of oxidation bases and couplers with an oxidizing agent, for example aqueous hydrogen peroxide solution, leaving the fibres to stand and then rinsing them. The colorations resulting therefrom are permanent, strong and resistant to external agents, especially to light, bad weather, washing, perspiration and rubbing.

Although these colorations produce strong, fast glints, the use of an oxidizing agent such as aqueous hydrogen peroxide solution, which is often in the presence of an alkaline agent, results in degradation of the keratin fibres.

There is thus a real need to find chromatic dyes which can dye human keratin fibres as strongly as oxidation dyes, which are just as light-stable as oxidation dyes, and which are also resistant to bad weather, washing and perspiration. There is also a real need to find dyes that can produce rises in colour comparable to those obtained with oxidation dye precursors. Furthermore, the Applicant has sought to obtain dyes with a good level of harmlessness that do not degrade keratin fibres.

The inventors have discovered that the use of latent pigments allows keratin fibres to be dyed strongly and in a very long-lasting manner, without, however, degrading them. These surprising performance qualities are obtained using latent pigments, which are molecules that are soluble in dye formulations, and which produce molecules that are very sparingly soluble or even insoluble in water when they are in keratin fibres.

Latent pigments are known substances. They have been described in patent application WO 98/32802, especially in the field of paints, inks and plastics.

A latent pigment is a compound that is insoluble, or only very sparingly soluble, in water (for instance a pigment), which has been converted so as to make it soluble in an aqueous formulation. Thus, the aqueous dye formulation containing the latent pigment is applied to the keratin fibres. After diffusing this soluble compound in the fibres, a "breaking" reaction is performed, leading to the formation of a substantially insoluble molecule, for the final pigment. These "breaking" reactions are known methods. They are thermal, chemical or photochemical reactions on the latent pigment, which is soluble. These reactions result in the breaking of the bond between the chromophoric radical and the solubilizing group(s). This breaking reaction may be considered as a reaction to regenerate a sparingly soluble original compound, and may be performed inside the keratin fibre.

One subject of the present invention is the use for dyeing keratin fibres, in particular human keratin fibres and more particularly the hair, of latent pigments. The invention also relates to a cosmetic composition comprising at least one latent pigment. Another subject of the invention is processes for dyeing keratin fibres using latent pigments, and also multi-compartment dyeing devices or "kits".

Other characteristics, aspects, subjects and advantages of the invention that are featured in the description below will allow the invention to be defined more clearly.

In accordance with the invention, use is made, for dyeing keratin fibres, in particular human keratin fibres and more particularly the hair, of latent pigments, which are soluble in a medium that is suitable for dyeing, and which can be chemically, thermally or photochemically converted in the fibres into water-insoluble pigments.

The latent pigment used according to the present invention is preferably represented by formula (I)

$$A(B)_x \qquad (I)$$

in which
x represents an integer ranging from 1 to 8,
A represents the chromophoric radical of dyes comprising a hetero atom chosen from N, O and S, and
when x=1, B represents a group of formula (II),
when x is greater than 1, B denotes a hydrogen atom or a group of formula (II),
B denoting at least once a group of formula (II),
the group of formula (II) corresponds to

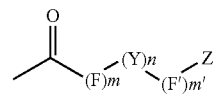

in which
Z represents a cationic water-solubilizing group $Z^+$ or a polyethylene glycol residue,
Y represents a hetero atom chosen from the group formed by N, O and S, Y preferably being O,
F and F' represent, independently of each other, a linear or branched $C_1$-$C_{14}$ alkylene chain, which may contain hetero atoms and may be substituted with one or more hydroxyl, amino or halogen groups,
n, m and m' denote, independently of each other, 0 or 1,
B being linked to a hetero atom chosen from the group N, O and S of the chromophore A.

$Z^+$ is preferably an aliphatic group, an aromatic group, a saturated or unsaturated carbocyclic group or a heterocyclic group and bears at least one quaternized nitrogen atom.

Preferably, the chromophore A is the radical of dyes such as perylene, quinacridone, dioxazine, isoindoline, indigo, bisisoindoline, phthalocyanin, pyrrolopyrrole, quinophthalone, azo, anthraquinone, indanthrone, isoindolinone, naphthoquinone, benzoquinone and azo-methine.

The term "halogen" means an element chosen from fluorine, chlorine, bromine and iodine.

More particularly, the chromophoric radical A is chosen from:

the perylene derivatives of formula (III) or (IV)

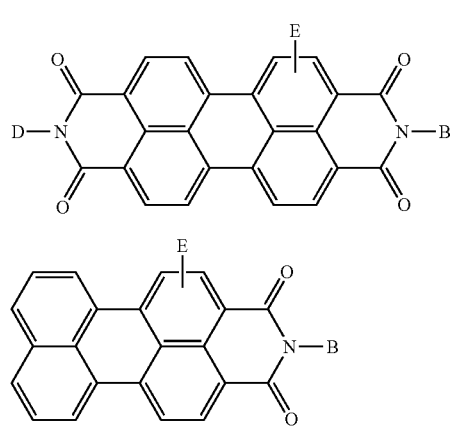

in which
D represents a hydrogen atom, a halogen atom, a linear or branched $C_1$-$C_{24}$ and preferably $C_1$-$C_6$ alkyl group, or a phenyl, benzyl or phenethyl group optionally substituted with a $C_1$-$C_6$ alkyl group, or a group of formula B,
E represents a hydrogen atom, a halogen atom, a linear or branched $C_1$-$C_{24}$ and preferably $C_1$-$C_6$ alkyl group, a $C_1$-$C_6$ alkoxy group or a phenyl group, the quinacridones of formula (V)

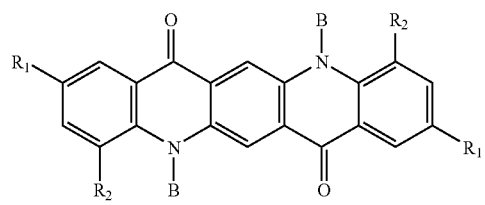

in which
$R_1$ and $R_2$, independently of each other, represent a hydrogen atom, a halogen atom, a linear or branched $C_1$-$C_{24}$ and preferably $C_1$-$C_6$ alkyl group, a $C_1$-$C_6$ alkoxy group or a phenyl group, the dioxazines of formula (VI) or (VII)

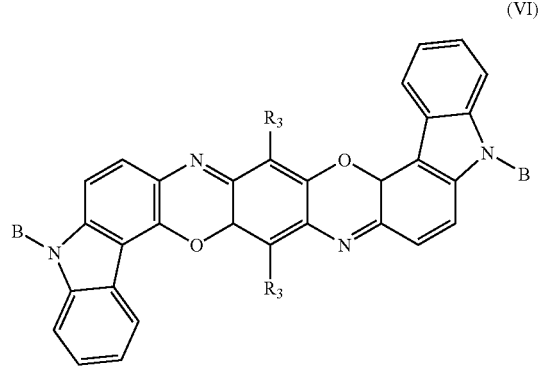

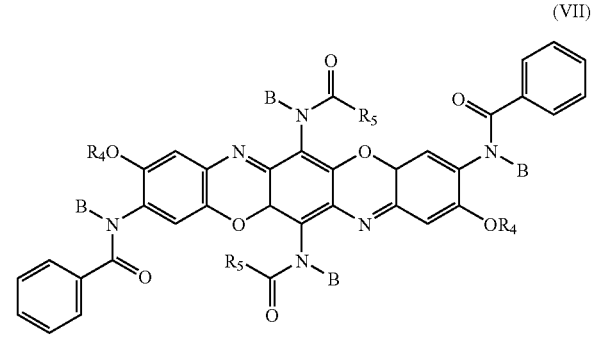

in which
$R_3$ represents a hydrogen atom, a halogen atom or a linear or branched $C_1$-$C_{24}$ and preferably $C_1$-$C_6$ alkyl group,
$R_4$ and $R_5$ each represent a $C_1$-$C_4$ alkyl group, the isoindolines of formula (VIII), (IX) or (X)

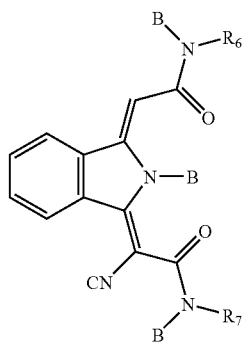

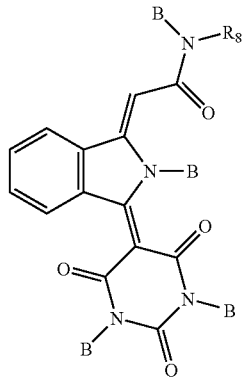

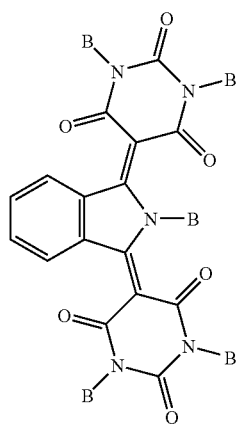
(X)

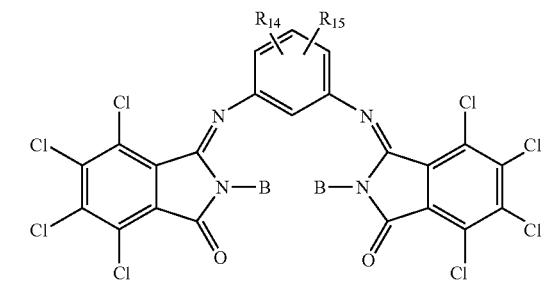
(XIV)

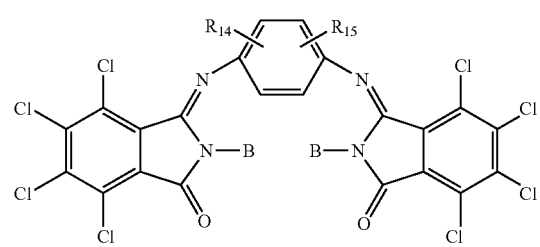
(XV)

in which
$R_6$ is represented by formula (XI),
$R_7$ represents a hydrogen atom, a linear or branched $C_1$-$C_{24}$ and preferably $C_1$-$C_6$ alkyl group, a benzyl group or a group of formula (XII),
$R_8$ represents a hydrogen atom, a group of formula (XI) or the group B,

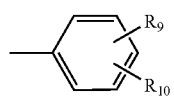
(XI)

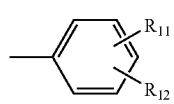
(XII)

$R_9$, $R_{10}$, $R_{11}$ and $R_{12}$, independently of each other, represent a hydrogen atom, a halogen atom, a linear or branched $C_1$-$C_{24}$ and preferably $C_1$-$C_6$ alkyl group, a $C_1$-$C_6$ alkoxy group or a trifluoromethyl group, the indigo derivatives of formula (XIII)

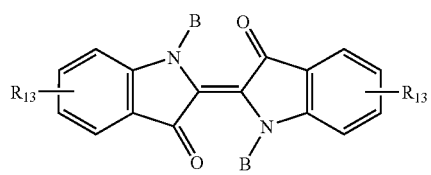
(XIII)

in which
$R_{13}$ represents a hydrogen atom, a halogen atom, a linear or branched $C_1$-$C_6$ alkyl group, a $C_1$-$C_6$ alkoxy group or a nitrile group, the bisisoindolinone derivatives of formula (XIV) or (XV)

in which
$R_{14}$ and $R_{15}$, independently of each other, represent a hydrogen atom, a halogen atom or a linear or branched $C_1$-$C_4$ alkyl group, the anthraquinoid derivatives of formula (XVI) or (XVII)

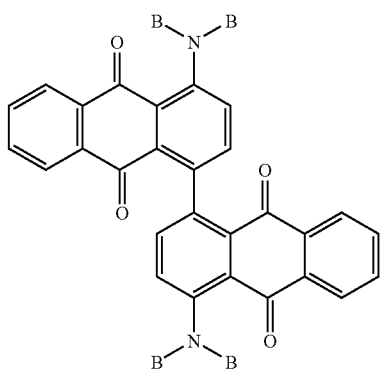
(XVI)

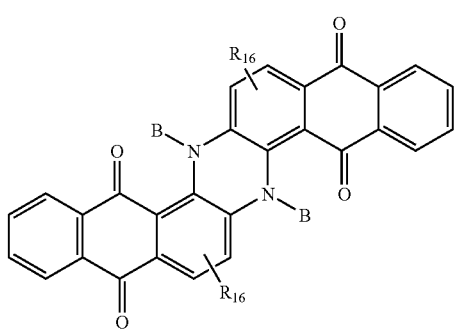
(XVII)

in which $R_{16}$ represents a hydrogen atom or a halogen atom, the phthalocyanin derivatives of formula (XVIII)

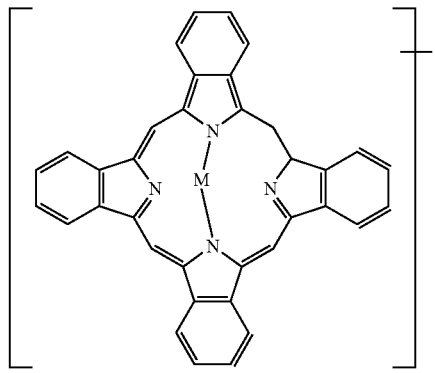

in which
M represents $H_2$, a divalent metal chosen from copper, magnesium, iron, zinc, aluminium, manganese, calcium and barium, or a divalent metallic group such as MnO or TiO, $T_1$ represents a group —$CHR_{18}$-, —CO— or —$SO_2$-, $R_{17}$ represents a hydrogen atom, a linear or branched $C_1$-$C_6$ alkyl group, a group —$N(B)R_{18}$, —$N(B)_2$, —$NHCOR_{19}$ or —$COR_{19}$, or a group of formula

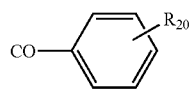

$R_{18}$ represents a hydrogen atom or a linear or branched $C_1$-$C_6$ alkyl group, $R_{19}$ represents a linear or branched $C_1$-$C_6$ alkyl group, $R_{20}$ represents a hydrogen atom, a halogen atom, a linear or branched $C_1$-$C_6$ alkyl group or a $C_1$-$C_6$ alkoxy group, z represents 0 or 1, y represents an integer from 1 to 8, the pyrrolopyrrole derivatives of formula (XIX) or (XX)

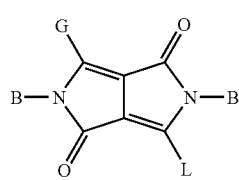

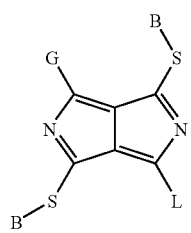

in which G and L, independently of each other, may have the meaning:

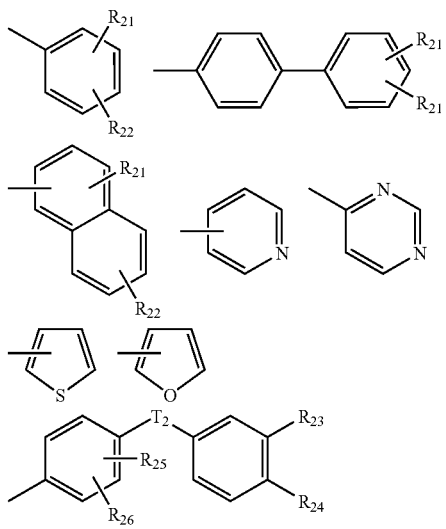

$R_{21}$ and $R_{22}$, independently of each other, represent a hydrogen atom, a halogen atom, a linear or branched $C_1$-$C_{24}$ and preferably $C_1$-$C_6$ alkyl group, a $C_1$-$C_6$ alkoxy group, a $C_1$-$C_{18}$ alkylthio group, a $C_1$-$C_{18}$ alkylamino group, a cyano, nitro, phenyl, trifluoromethyl or $C_5$-$C_6$ cycloalkyl group, a group —C=N—($C_1$-$C_{24}$ and preferably $C_1$-$C_6$ alkyl), a group of formula

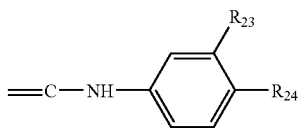

an imidazolyl, pyrazolyl, triazolyl, piperazinyl, pyrrolyl, oxazolyl, benzoxazolyl, benzothiazolyl, benzimidazolyl, morpholinyl, piperidyl or pyrrolidinyl radical, $T_2$ represents —$CH_2$—, —$CH(CH_3)$—, —$C(CH_3)_2$—, —CH=N—, —N=N—, —O—, —S—, —SO—, —$SO_2$— or —$NHR_{27}$, $R_{23}$ and $R_{24}$, independently of each other, represent a hydrogen atom, a halogen, a linear or branched $C_1$-$C_6$ alkyl group, a $C_1$-$C_6$ alkoxy group or —CN, $R_{25}$ and $R_{26}$, independently of each other, represent a hydrogen atom, a halogen atom or a linear or branched $C_1$-$C_6$ alkyl group, $R_{27}$ represents a hydrogen atom or a linear or branched $C_1$-$C_6$ alkyl group, the quinophthalone derivatives of formula (XXI) or (XXII)

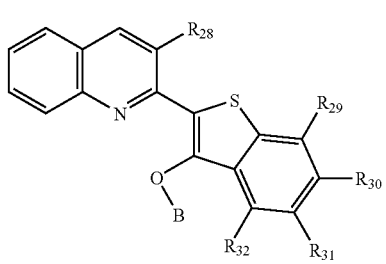

-continued
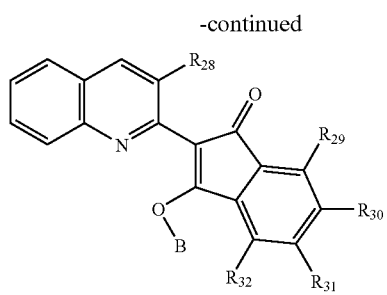
(XXII)
in which
$R_{28}$ represents a hydrogen atom or a group OB,
$R_{29}$, $R_{30}$, $R_{31}$ and $R_{32}$, independently of each other, represent a hydrogen atom, a halogen atom, a linear or branched $COO(C_1$-$C_6)$alkyl group or a linear or branched $CONH(C_1$-$C_6)$alkyl group,
the azo compounds of formulae (XXIII) to (XXVIII)
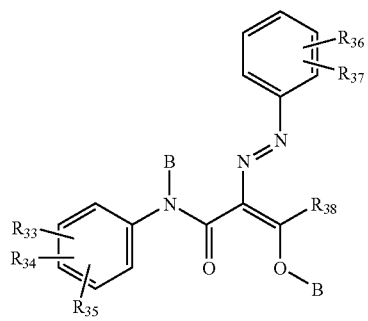
(XXIII)
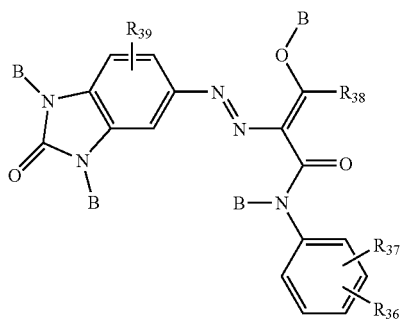
(XXIV)
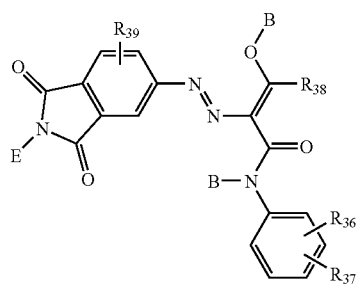
(XXV)
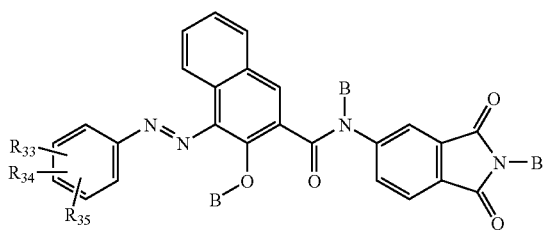
(XXVI)
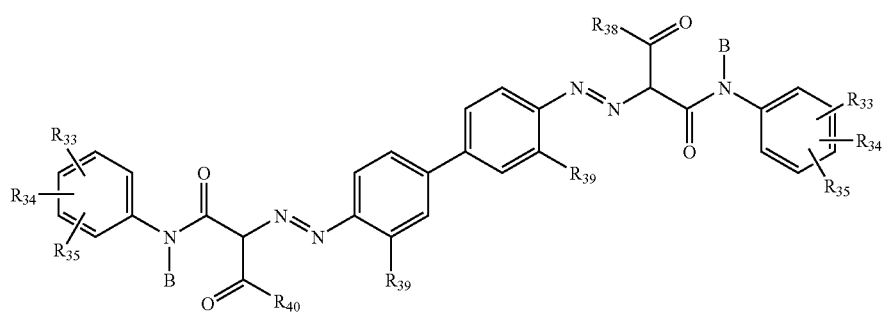
(XXVII)

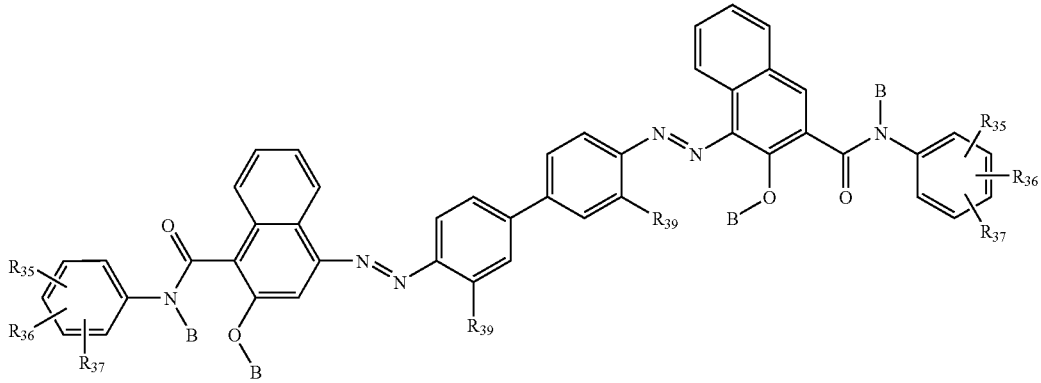 (XXVIII)

in which $R_{33}$, $R_{34}$, $R_{35}$, $R_{36}$, $R_{37}$, $R_{38}$ and $R_{40}$, independently of each other, each represent a hydrogen atom, a halogen atom, a linear or branched $C_1$-$C_6$ alkyl group, a $C_1$-$C_6$ alkoxy group, a nitro or acetyl group or an $SO_2NH(C_1$-$C_6)$alkyl group, $R_{39}$ represents a hydrogen atom, a halogen atom, a linear or branched $C_1$-$C_6$ alkyl group or a $C_1$-$C_6$ alkoxy group, the anthraquinone derivatives of formula (XXIX) or (XXX)

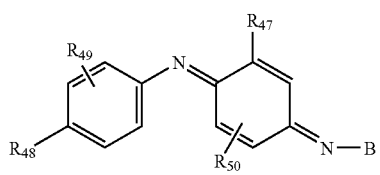 (XXIX)

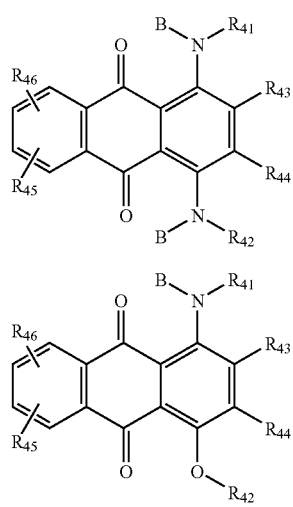 (XXX)

in which $R_{41}$ and $R_{42}$, independently of each other, represent a hydrogen atom, a halogen atom, a linear or branched $C_1$-$C_{12}$ alkyl group, a $C_1$-$C_6$ alkoxy group or a $C_6$-$C_{12}$ aryl group, which is unsubstituted or substituted with one or more halogen atoms, one or more linear or branched $C_1$-$C_6$ alkyl, nitro or acetyl groups, or a group $SO_2NH$-$(C_1$-$C_6)$alkyl or $SO_2NH_2$, $R_{43}$ and $R_{44}$, independently of each other, represent a hydrogen atom, a halogen atom, a linear or branched $C_1$-$C_6$ alkyl group, a $C_1$-$C_6$ alkoxy group, a nitro, cyano, $CONH_2$, $SO_2NH(C_1$-$C_6)$alkyl, $SO_2NH_2$, $SO_3H$ or $SO_3Na$ group or a $C_6$-$C_{12}$ aryl group, which is unsubstituted or substituted with one or more halogen atoms, one or more linear or branched $C_1$-$C_6$ alkyl, nitro, acetyl or $SO_2NH(C_1$-$C_6)$alkyl groups or with $SO_2NH_2$, $R_{45}$ and $R_{46}$ represent, independently of each other, a hydrogen atom, a halogen atom, a $C_1$-$C_6$ alkoxy group or a nitro, cyano, hydroxyl or amino group, the azomethine derivatives of formula (XXXI)

 (XXXI)

$R_{47}$, $R_{48}$, $R_{49}$ and $R_{50}$, independently of each other, represent a hydrogen atom, a halogen atom, a linear or branched $C_1$-$C_6$ alkyl group, a $C_1$-$C_6$ alkoxy group, a nitro, cyano, $CONH_2$, $SO_2NH$-$(C_1$-$C_6)$alkyl, $SO_2NH_2$, $SO_3H$ or $SO_3Na$ group or a $C_6$-$C_{12}$ aryl group, which is unsubstituted or substituted with one or more halogen atoms, one or more linear or branched $C_1$-$C_6$ alkyl, nitro, acetyl or $SO_2NH(C_1$-$C_6)$alkyl groups or with $SO_2NH_2$.

The cosmetic compositions in accordance with the invention contain at least one latent pigment and at least one compound chosen from acidifying agents, surfactants, monoalcohols and polyols that are liquid at 25° C.

The acidifying agents in the compositions of the invention may be mineral or organic. In the latter case, the functions providing the acidity may be sulphonic or carboxylic groups. As acidifying agents that may be used according to the invention, mention may be made of hydrochloric acid, citric acid, lactic acid and tartaric acid.

The concentration of acidifying agents may range from 0.0001% to 20% and preferably from 0.01% to 10% of the total weight of the compositions.

The monoalcohols or polyols that are liquid at 25° C. in the compositions according to the invention are saturated or unsaturated. They are preferably chosen from ethanol, isopropanol, propylene glycol, glycerol, hexylene glycol, isoprene glycol, dipropylene glycol, neopentyl glycol, 3-methyl-1,3,5-pentanetriol, 1,2,4-butanediol, 1,5-pentanediol, 2-methyl-1,3-propanediol, 3-methyl-1,5-pentanediol, polyethylene glycols and benzyl alcohol.

Their concentration may be between 0.05% and 50% and preferably between 0.1% and 20% of the total weight of the composition.

The surfactants may be of anionic, nonionic, cationic or amphoteric nature. The surfactants that are suitable for use in the present invention are especially the following:

(i) Anionic Surfactant(s):

By way of example of anionic surfactants that can be used, alone or as mixtures, in the context of the present invention, mention may be made in particular (nonlimiting list) of salts (in particular alkali metal salts, especially sodium salts, ammonium salts, amine salts, amino alcohol salts or magnesium salts) of the following compounds: alkyl sulphates, alkyl ether sulphates, alkylamido ether sulphates, alkylaryl polyether sulphates, monoglyceride sulphates; alkyl sulphonates, alkyl phosphates, alkylamide sulphonates, alkylaryl sulphonates, α-olefin sulphonates, paraffin sulphonates; $(C_6-C_{24})$ alkyl sulphosuccinates, $(C_6-C_{24})$alkyl ether sulphosuccinates, $(C_6-C_{24})$alkylamide sulphosuccinates; $(C_6-C_{24})$alkyl sulphoacetates; $(C_6-C_{24})$acyl sarcosinates and $(C_6-C_{24})$acyl glutamates. It is also possible to use $(C_6-C_{24})$alkylpolyglycoside carboxylic esters such as alkylglucoside citrates, alkylpolyglycoside tartrates and alkylpolyglycoside sulphosuccinates, alkylsulphosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactosiduronic acids and their salts, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and their nature is not a critical factor in the context of the present invention. Thus, they can be chosen in particular from (nonlimiting list) polyethoxylated or polypropoxylated alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides. It will be noted that alkylpolyglycosides are nonionic surfactants that are particularly suitable within the context of the present invention.

(iii) Amphoteric or Zwitterionic Surfactant(s):

The amphoteric or zwitterionic surfactants, the nature of which is not a critical factor in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulphonate, sulphate, phosphate or phosphonate); mention may also be made of $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

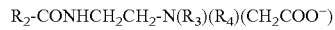

$R_2$-CONHCH$_2$CH$_2$-N(R$_3$)(R$_4$)(CH$_2$COO$^-$)

in which: $R_2$ denotes a linear or branched $C_5$-$C_{20}$ alkyl radical derived from an acid $R_2$—COOH present, for example, in hydrolysed coconut oil, a heptyl, nonyl or undecyl radical, $R_3$ denotes a beta-hydroxyethyl group and $R_4$ denotes a carboxymethyl group; and

$R_2'$-CONHCH$_2$CH$_2$-N(B)(C)

in which:

B represents —CH$_2$CH$_2$OX', C represents —(CH$_2$)$_z$-Y', with z=1 or 2,

X' denotes the —CH$_2$CH$_2$—COOH group or a hydrogen atom,

Y' denotes —COOH or the —CH$_2$—CHOH-SO$_3$H radical, $R_2'$ denotes a saturated or unsaturated, linear or branched $C_5$-$C_{20}$ alkyl radical of an acid $R'_2$—COOH present for example in coconut oil or in hydrolysed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ alkyl radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name Miranol® C2M Concentrate by the company Rhodia Chimie.

(iv) Cationic Surfactants:

Among the cationic surfactants, mention may be made in particular (nonlimiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

Their concentration may be between 0.05% and 50% and preferably between 0.2% and 25% of the total weight of the composition.

The medium that is suitable for dyeing, also known as the dye support, is preferably an aqueous medium containing at least one of the above ingredients.

Preferably, the compositions according to the invention have a pH of <7.

Standard cosmetic adjuvants used in dye compositions, such as antioxidants, penetrating agents, sequestering agents, fragrances, buffers, dispersants, film-forming agents, ceramides, preserving agents, opacifiers, vitamins or provitamins, nonionic, cationic, anionic or amphoteric polymers, and associative or non-associative mineral or organic thickeners, may be used in the compositions.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

Another subject of the invention relates to a process for dyeing keratin fibres, in particular human keratin fibres and more particularly the hair, using latent pigments.

In a first stage, a composition containing, in a medium that is suitable for dyeing, at least one latent pigment used according to the invention is applied to the keratin fibres.

The dye composition is left to act for a leave-in time ranging from 1 to 60 minutes and preferably from 10 to 45 minutes.

The fibres are then optionally rinsed.

The latent pigment on the said fibres is then treated thermally, chemically or photochemically so as to regenerate the sparingly soluble original compound. Preferably, the latter treatment is performed by means of a jump in pH. The solution used makes it possible to achieve a pH of greater than 7. An aqueous ammonia, alkanolamine, alkaline hydroxide or alkaline carbonate solution may be used.

Finally, steps of washing with shampoo and drying are performed.

The invention also relates to a two-compartment device for dyeing the fibres. The first compartment of this device contains a dye composition containing, in a medium that is suitable for dyeing, at least one latent pigment used according to the invention, and the second compartment contains a solution of a chemical agent capable of rendering insoluble the latent pigment as the sparingly soluble original compound. The second compartment will preferably contain a solution for achieving a pH of greater than 7.

The example that follows is intended to illustrate the invention without being limiting in nature.

EXAMPLE

The Applicant prepared a composition containing compound A shown below.

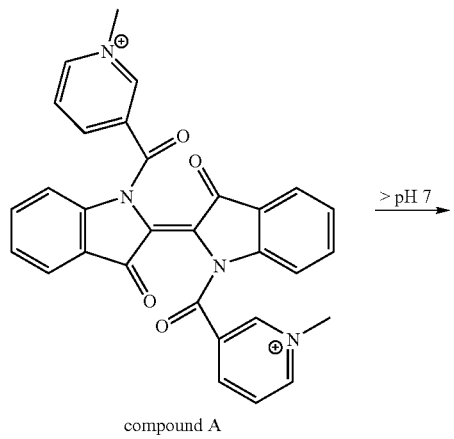

compound A

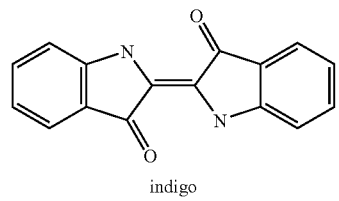

indigo

The composition containing compound A was formulated as follows:

| Dye formulation | |
|---|---|
| Natrosol 250MR (hydroxyethylcellulose) | 0.72 g |
| NIPA ester 82121 (mixture of methyl, butyl, ethyl, propyl and isobutyl p-hydroxybenzoates) | 0.06 g |
| Oramix CG 110 ((50/50 C8/C10) alkyl polyglucoside (2) as a buffered aqueous 60% solution) | 5 g |
| Benzyl alcohol | 4 g |
| Polyethylene glycol 400 (polyethylene glycol (8 EO)) | 6 g |
| Compound A | 0.3 g |
| Citric acid | qs pH 4 |
| Water | qs |

The composition was applied to lightly bleached hair with a bath ratio of 10.

After a leave-in time of 30 minutes, a dilute triethanolamine solution was applied to the lock. The regeneration reaction was thus performed by means of a jump in pH. The colour of the lock then changed from violet to blue.

The lock was then shampooed and dried. It was blue and the coloration showed a very good level of fastness.

The invention claimed is:

1. A process for dyeing human keratin fibers, comprising:
   applying to the keratin fibers a composition comprising at least one latent pigment, wherein said at least one latent pigment is soluble in a medium that is suitable for dyeing, and then chemically, thermally or photochemically converting the latent pigment in the keratin fibres into a water-insoluble pigment,
   wherein said at least one latent pigment is chosen from those of formula (I):

A(B)$_x$       (I)

wherein:
   x is an integer ranging from 1 to 8,
   A is a dye radical chosen from perylene, quinacridone, dioxazine, isoindoline, indigo, bisisoindoline, phthalocyanin, pyrrolopyrrole, quinophthalone, anthraquinone, indanthrone, isoindolinone, naphthoquinone, benzoquinone and azomethine radicals, wherein
   when x is equal to 1, B is chosen from groups of formula (II), and
   when x is greater than 1, B is chosen from a hydrogen atom and groups of formula (II), with the proviso that when x is greater than 1, B is at least one chosen from the groups of formula (II):

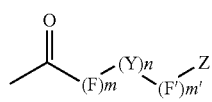
(II)

wherein

Z is chosen from cationic water-solubilizing groups $Z^+$ and polyethylene glycol residues, Y is a hetero atom chosen from N, O and S, F and F', which can be identical or different, are chosen from linear and branched $C_1$-$C_{14}$ alkylene chains, which optionally comprise hetero atoms and are optionally substituted with at least one entity chosen from hydroxyl radicals, amino radicals, and halogens, n, m and m', which may be identical or different, are chosen from zero and 1, and B is linked to a hetero atom of the dye radical A.

2. The process according to claim 1, wherein Y is oxygen.

3. The process according to claim 1, wherein $Z^{30}$ is chosen from aliphatic groups, aromatic groups, saturated and unsaturated carbocyclic groups and heterocyclic groups, and wherein $Z^+$ bears at least one quaternized nitrogen atom.

4. The process according to claim 1, wherein the perylene radicals are chosen from those of formulae (III) and (IV):

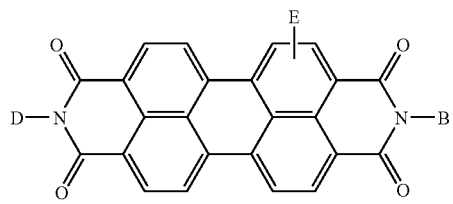
(III)

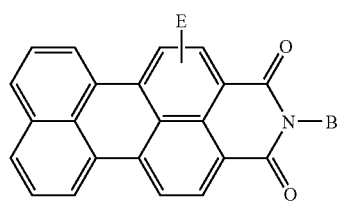
(IV)

wherein:

D is chosen from a hydrogen atom, halogens, linear and branched $C_1$-$C_{24}$ alkyl groups, phenyl, benzyl and phenethyl groups optionally substituted with a $C_1$-$C_6$ alkyl group, and the groups of B, E is chosen from a hydrogen atom, halogens, linear and branched $C_1$-$C_{24}$ alkyl groups, $C_1$-$C_6$ alkoxy groups and phenyl groups, and B is chosen from a hydrogen atom and groups of formula (II), with the proviso that at least one B is a group of formula (II).

5. The process according to claim 1, wherein the quinacridone radicals are chosen from those of formula (V):

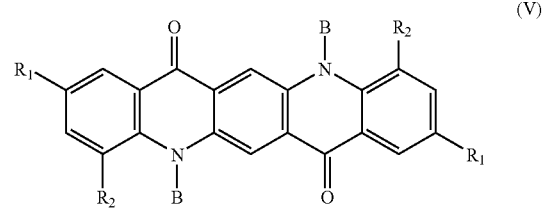
(V)

wherein $R_1$ and $R_2$, which may be identical or different, are chosen from hydrogen atoms, halogens, linear and branched $C_1$-$C_{24}$ alkyl groups, $C_1$-$C_6$ alkoxy groups and phenyl groups, and B is chosen from a hydrogen atom and groups of formula (II), with the proviso that at least one B is a group of formula (II).

6. The process according to claim 1, wherein the dioxazine radicals are chosen from those of formulae (VI) and (VII):

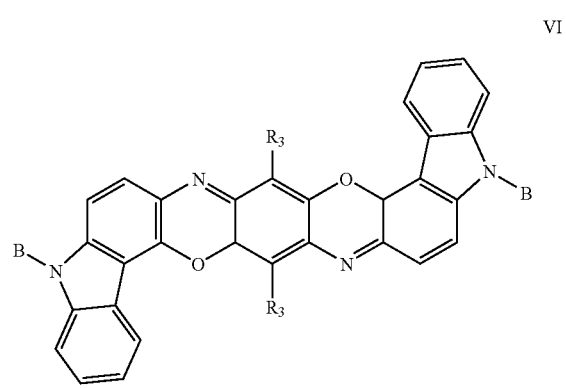
VI

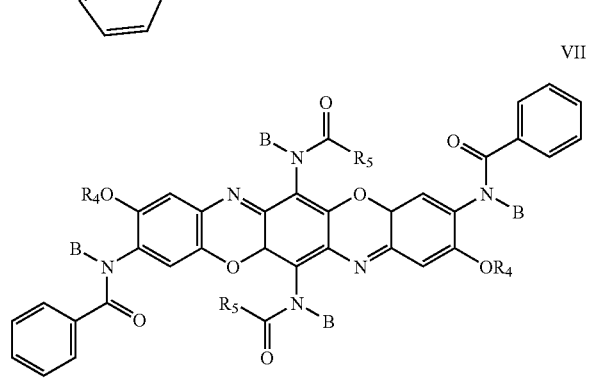
VII wherein $R_3$ is chosen from a hydrogen atom, halogens, and linear and branched $C_1$-$C_{24}$ alkyl groups, $R_4$ and $R_5$, which may be identical or different, are chosen from $C_1$-$C_4$ alkyl groups, and B is chosen from a hydrogen atom and groups of formula (II), with the proviso that at least one B per formula is a group of formula (II).

7. The process according to claim 1, wherein the isoindoline radicals are chosen from those of formulae (VIII), (IX) and (X):

(VIII)

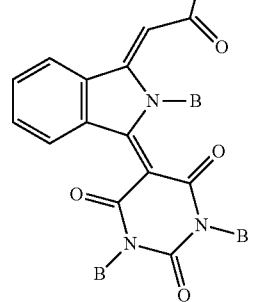

(IX)

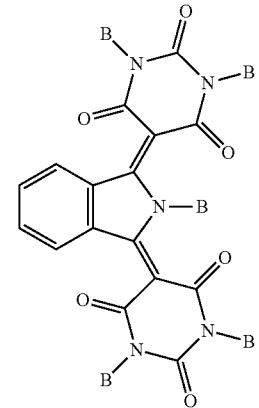

(X)

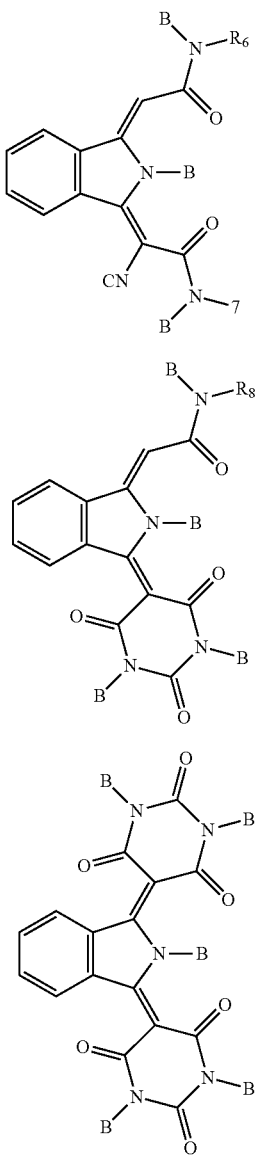

wherein
$R_6$ is chosen from groups of formula (XI),
$R_7$ is chosen from a hydrogen atom, linear and branched $C_1$-$C_{24}$ alkyl groups, benzyl groups, and groups of formula (XII),
$R_8$ is chosen from a hydrogen atom, groups of formula (XI), and the group B, (XI)

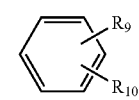

(XII)

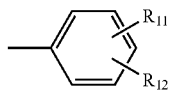

$R_9$, $R_{10}$, $R_{11}$ and $R_{12}$, which may be identical or different, are chosen from a hydrogen atom, halogens, linear and branched $C_1$-$C_{24}$ alkyl groups, $C_1$-$C_6$ alkoxy groups and trifluoromethyl groups, and B is chosen from a hydrogen atom and groups of formula (II), with the proviso that at least one B per formula is a group of formula (II).

8. The process according to claim 1, wherein the indigo radicals are chosen from those of formula (XIII):

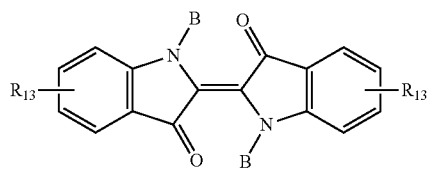

(XIII)

wherein $R_{13}$ is chosen from a hydrogen atom, halogens, linear and branched $C_1$-$C_6$ alkyl groups, $C_1$-$C_6$ alkoxy groups and nitrile groups, and B is chosen from a hydrogen atom and groups of formula (II), with the proviso that at least one B per formula is a group of formula (II).

9. The process according to claim 1, wherein the bisindolinone radicals are chosen from those of formulae (XIV) and (XV):

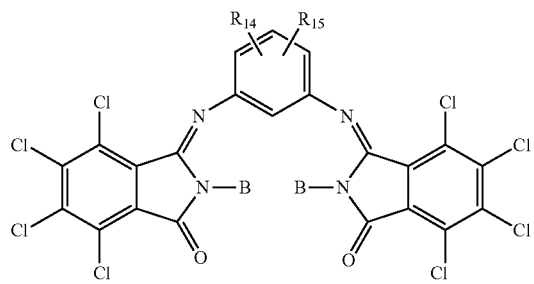

(XIV)

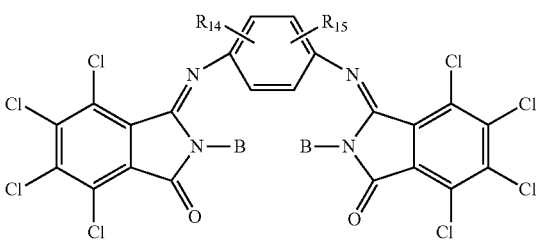

(XV)

wherein $R_{14}$ and $R_{15}$, which may be identical or different, are chosen from a hydrogen atom, halogens, and linear and branched $C_1$-$C_4$ alkyl groups, and B is chosen from a hydrogen atom and groups of formula (II), with the proviso that at least one B per formula is a group of formula (II).

10. The process according to claim 1, wherein the anthraquinoid radicals are chosen from those of formulae (XVI) and (XVII):

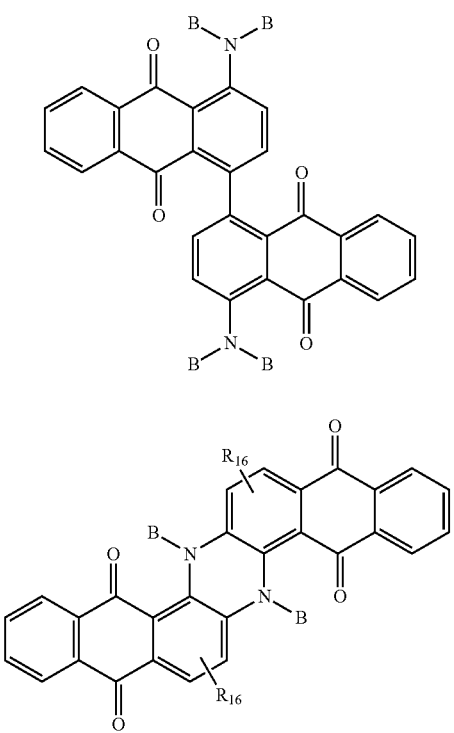

(XVI)

(XVII)

wherein $R_{16}$ is chosen from a hydrogen atom and halogens, and

B is chosen from a hydrogen atom and groups of formula (II), with the proviso that at least one B per formula is a group of formula (II).

11. The process according to claim 1, wherein the phthalocyanin radicals are chosen from those of formula (XVIII):

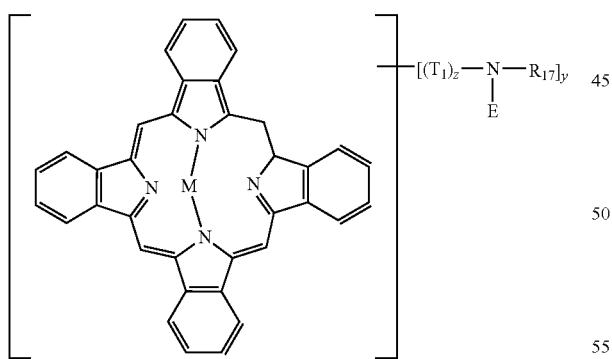

(XVIII)

wherein

M is chosen from $H_2$, divalent metals chosen from copper, magnesium, iron, zinc, aluminium, manganese, calcium and barium, and divalent metallic groups, $T_1$ is chosen from —$CHR_{18}$—, —CO— and —$SO_2$— groups, $R_{17}$ is chosen from a hydrogen atom, linear and branched $C_1$-$C_6$ alkyl groups, —N(B)$R_{18}$ groups, —N(B)$_2$ groups, —NHCOR$_{19}$ groups, —COR$_{19}$ groups, and groups of formula:

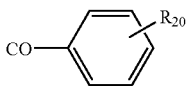

$R_{18}$ is chosen from a hydrogen atom and linear and branched $C_1$-$C_6$ alkyl groups, $R_{19}$ is chosen from linear and branched $C_1$-$C_6$ alkyl groups, $R_{20}$ is chosen from a hydrogen atom, halogens, linear and branched $C_1$-$C_6$ alkyl groups and $C_1$-$C_6$ alkoxy groups, wherein z is equal to zero or 1, y is an integer ranging from 1 to 8, and B is chosen from a hydrogen atom and groups of formula (II), with the proviso that at least one B per formula is a group of formula (II).

12. The process according to claim 11, wherein the divalent metallic groups are MnO and TiO.

13. The process according to claim 1, wherein the pyrrolopyrrole radicals are chosen from those of formulae (XIX) and (XX):

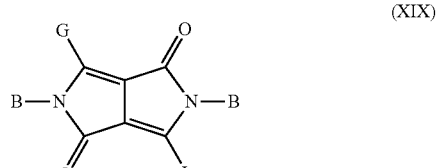

(XIX)

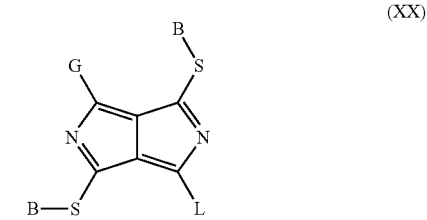

(XX)

wherein G and L, which may be identical or different, are chosen from the groups:

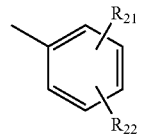 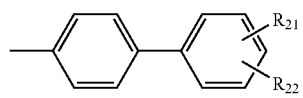

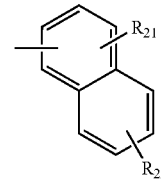 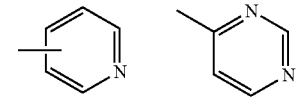

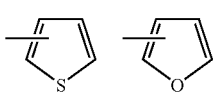 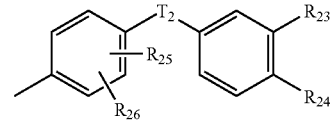

wherein $R_{21}$ and $R_{22}$, which may be identical or different, are chosen from hydrogen atoms, halogens, linear and branched $C_1$-$C_{24}$ alkyl groups, $C_1$-$C_6$ alkoxy groups, $C_1$-$C_{18}$ alkylthio groups, $C_1$-$C_{18}$ alkylamino groups, cyano groups, nitro groups, phenyl groups, trifluoromethyl groups, $C_5$-$C_6$ cycloalkyl groups, —C≡N— groups, groups of formula:

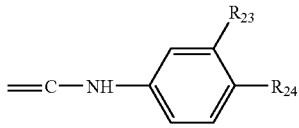

and imidazolyl, pyrazolyl, triazolyl, piperazinyl, pyrrolyl, oxazolyl, benzoxazolyl, benzothiazolyl, benzimidazolyl, morpholinyl, piperidyl and pyrrolidinyl radicals, wherein $T_2$ is chosen from —$CH_2$—, —$CH(CH_3)$—, —$C(CH_3)_2$—, —CH=N—, —N=N—, —SO—, —$SO_2$— and —$NHR_{27}$ radicals, and oxygen and sulfur atoms, $R_{23}$ and $R_{24}$, which may be identical or different, are chosen from hydrogen atoms, halogens, linear and branched $C_1$-$C_6$ alkyl groups, $C_1$-$C_6$ alkoxy groups, and —CN groups, $R_{25}$ and $R_{26}$, which may be identical or different, are chosen from hydrogen atoms, halogens, and linear and branched $C_1$-$C_6$ alkyl groups, $R_{27}$ is chosen from a hydrogen atom and linear and branched $C_1$-$C_6$ alkyl groups, and B is chosen from a hydrogen atom and groups of formula (II), with the proviso that at least one B per formula is a group of formula (II).

14. The process according to claim 1, wherein the quinophthalone radicals are chosen from those of formulae (XXI) and (XXII):

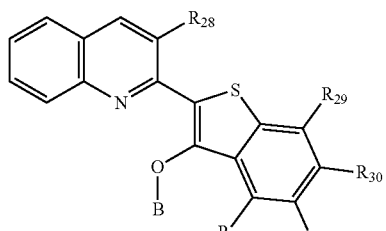

(XXI)

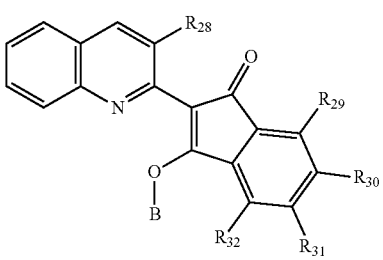

(XXII)

wherein $R_{28}$ is chosen from a hydrogen atom and OB groups, $R_{29}$, $R_{30}$, $R_{31}$ and $R_{32}$, which may be identical or different, are chosen from hydrogen atoms, halogens, linear and branched COO($C_1$-$C_6$)alkyl groups, and linear and branched CONH($C_1$-$C_6$)alkyl groups, and B is chosen from a hydrogen atom and groups of formula (II), with the proviso that at least one B per formula is a group of formula (II).

15. The process according to claim 1, wherein the anthraquinone derivatives are chosen from those of formulae (XXIX) and (XXX):

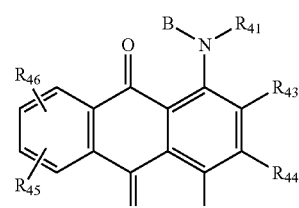

(XXIX)

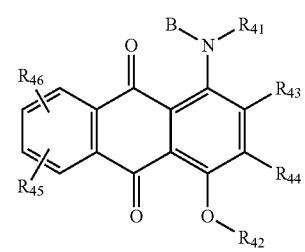

(XXX)

wherein:

$R_{41}$ and $R_{42}$, which may be identical or different, are chosen from hydrogen atoms, halogens, linear and branched $C_1$-$C_{12}$ alkyl groups, $C_1$-$C_6$ alkoxy groups, $C_6$-$C_{12}$ aryl groups that are unsubstituted or substituted with at least one entity chosen from halogens, linear and branched $C_1$-$C_6$ alkyl groups, nitro groups, acetyl groups, $SO_2NH$ ($C_1$-$C_6$)alkyl groups and $SO_2NH_2$ groups, $R_{43}$ and $R_{44}$, which may be identical or different, are chosen from hydrogen atoms, halogens, linear and branched $C_1$-$C_6$ alkyl groups, $C_1$-$C_6$ alkoxy groups, nitro groups, cyano groups, $CONH_2$ groups, $SO_2NH(C_1$-$C_6$)alkyl groups, $SO_2NH_2$ groups, $SO_3H$ groups, $SO_3Na$ groups, and $C_6$-$C_{12}$ aryl groups that are unsubstituted or substituted with at least one entity chosen from halogens, linear and branched $C_1$-$C_6$ alkyl groups, nitro groups, acetyl groups, $SO_2NH(C_1$-$C_6$)alkyl groups and $SO_2NH_2$ groups, $R_{45}$ and $R_{46}$, which may be identical or different, are chosen from hydrogen atoms, halogens, $C_1$-$C_6$ alkoxy groups, and nitro, cyano, hydroxyl and amino groups, and B is chosen from a hydrogen atom and groups of formula (II), with the proviso that at least one B per formula is a group of formula (II).

16. The process according to claim 1, wherein the azomethine radicals are chosen from those of formula (XXXI):

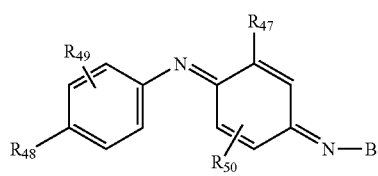

(XXXI)

wherein

R$_{47}$, R$_{48}$, R$_{49}$ and R$_{50}$, which may be identical or different, are chosen from hydrogen atoms, halogens, linear and branched C$_1$-C$_6$ alkyl groups, C$_1$-C$_6$ alkoxy groups, nitro groups, cyano groups, CONH$_2$ groups, SO$_2$NH (C$_1$-C$_6$)alkyl groups, SO$_2$NH$_2$ groups, SO$_3$H groups, SO$_3$Na groups, and C$_6$-C$_{12}$ aryl groups that are unsubstituted or substituted with at least one entity chosen from halogens, linear and branched C$_1$-C$_6$ alkyl groups, nitro groups, acetyl groups, SO$_2$NH(C$_1$-C$_6$)alkyl groups, and SO$_2$NH$_2$ groups, and B is chosen from groups of formula (II).

17. A process for dyeing human keratin fibers, comprising:
(i) applying to the keratin fibers a composition comprising, in a medium that is suitable for dyeing, at least one latent pigment, wherein the at least one latent pigment is soluble in a medium that is suitable for dyeing, and is capable of being chemically, thermally or photochemically converted in the keratin fibers into water-insoluble pigments,
(ii) leaving the dye composition to act on the keratin fibers for a leave-in time ranging from 1 to 60 minutes,
(iii) optionally rinsing the hair, and then converting the at least one latent pigment to an at least one water-insoluble pigment in a manner chosen from thermal, chemical and photochemical treatment,
(iv) washing the treated fibers with shampoo, and drying;
wherein said at least one latent pigment is chosen from those of formula (I):

$$A(B)_x \qquad (I)$$

wherein:
x is an integer ranging from 1 to 8,
A is a dye radical chosen from perylene, quinacridone, dioxazine, isoindoline, indigo, bisisoindoline, phthalocyanin, pyrrolopyrrole, quinophthalone, anthraquinone, indanthrone, isoindolinone, naphthoquinone, benzoquinone and azomethine radicals, wherein
when x is equal to 1, B is chosen from groups of formula (II), and
when x is greater than 1, B is chosen from a hydrogen atom and groups of formula (II), with the proviso that when x is greater than 1, B is at least once chosen from the groups of formula (II):

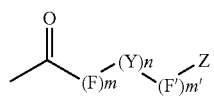

(II)

wherein:
Z is chosen from cationic water-solubilizing groups Z$^+$ and polyethylene glycol residues,
Y is a hetero atom chosen from N, O and S,
F and F', which can be identical or different, are chosen from linear and branched C$_1$-C$_{14}$ alkylene chains, which optionally comprise hetero atoms and are optionally substituted with at least one entity chosen from hydroxyl radicals, amino radicals, and halogens,
n, m and m', which may be identical or different, are chosen from zero and 1, and
B is linked to a hetero atom of the dye radical A.

18. The process according to claim 17, wherein the at least one latent pigment is chemically converted to at least one water-insoluble pigment via an increase in pH.

19. The process according to claim 18, wherein the at least one latent pigment in the keratin fibers is treated with a solution of an alkaline compound.

20. The process according to claim 19, wherein the alkaline compound is chosen from aqueous ammonia, alkanolamines, alkaline hydroxides and alkaline carbonates.

21. A cosmetic composition for dyeing human keratin fibers comprising at least one latent pigment and at least one compound chosen from monoalcohols and polyols that are liquid at 25° C., acidifying agents and surfactants,
wherein the at least one latent pigment is capable of being chemically, thermally or photochemically converted in the keratin fibers into an at least one water-insoluble pigment, and
wherein said at least one latent pigment is chosen from those of formula (I):

$$A(B)_x \qquad (I)$$

wherein:
x is an integer ranging from 1 to 8,
A is a dye radical chosen from perylene, quinacridone, dioxazine, isoindoline, indigo, bisisoindoline, phthalocyanin, pyrrolopyrrole, quinophthalone, anthraquinone, indanthrone, isoindolinone, naphthoquinone, benzoquinone and azomethine radicals, wherein
when x is equal to 1, B is chosen from groups of formula (II), and
when x is greater than 1, B is chosen from a hydrogen atom and groups of formula (II), with the proviso that when x is greater than 1, B is at least once chosen from the groups of formula (II):

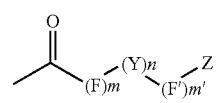

(II)

wherein
Z is chosen from cationic water-solubilizing groups Z$^+$ and polyethylene glycol residues,
Y is a hetero atom chosen from N, O and S,
F and F', which can be identical or different, are chosen from linear and branched C$_1$-C$_{14}$ alkylene chains, which optionally comprise hetero atoms and are optionally substituted with at least one entity chosen from hydroxyl radicals, amino radicals, and halogens,
n, m and m', which may be identical or different, are chosen from zero and 1, and
B is linked to a hetero atom of the dye radical A.

22. The composition according to claim 21, wherein Y is oxygen.

23. The composition according to claim 21, wherein Z$^+$ is chosen from aliphatic groups, aromatic groups, saturated and unsaturated carbocyclic groups and heterocyclic groups, and wherein Z$^+$ bears at least one quaternized nitrogen atom.

24. The composition according to claim 21, wherein the acidifying agents are chosen from mineral and organic acidifying agents.

25. The composition according to claim 21, wherein the surfactants are chosen from nonionic, anionic, cationic and amphoteric surfactants.

26. The composition according to claim 21, wherein the at least one compound is chosen from acidifying agents and is present in the composition in an amount ranging from 0.0001% to 20% by weight, relative to the total weight of the composition.

27. The composition according to claim 21, wherein the at least one compound is chosen from surfactants and is present in a total amount ranging from 0.05% to 50% by weight, relative to the total weight of the composition.

28. The composition according to claim 21, wherein the at least one compound is chosen from monoalcohols and polyols that are liquid at 25° C. and is present in a total amount ranging from 0.05% to 50% by weight, relative to the total weight of the composition.

29. The composition according to claim 21, wherein said composition has a pH less than 7.

30. A kit for dyeing human keratin fibres, comprising at least two compartments, wherein the at least one first compartment comprises a dye composition comprising, in a medium that is suitable for dyeing, at least one latent pigment and at least one compound chosen from monoalcohols and polyols that are liquid at 25° C., acidifying agents and surfactants, wherein the at least one latent pigment is capable of being chemically, thermally or photochemically converted in the keratin fibres into an at least one water-insoluble pigment, wherein said at least one latent pigment is chosen from those of formula (I):

wherein:
x is an integer ranging from 1 to 8,
A is a dye radical chosen from perylene, quinacridone, dioxazine, isoindoline, indigo, bisisoindoline, phthalocyanin, pyrrolopyrrole, quinophthalone, anthraquinone, indanthrone, isoindolinone, naphthoquinone, benzoquinone and azomethine radicals,
wherein
when x is equal to 1, B is chosen from groups of formula (II), and
when x is greater than 1, B is chosen from a hydrogen atom and groups of formula (II), with the proviso that when x is greater than 1, B is at least once chosen from the groups of formula (II):

wherein
Z is chosen from cationic water-solubilizing groups $Z^+$ and polyethylene glycol residues,
Y is a hetero atom chosen from N, O and S,
F and F', which can be identical or different, are chosen from linear and branched $C_1$-$C_{14}$ alkylene chains, which optionally comprise hetero atoms and are optionally substituted with at least one entity chosen from hydroxyl radicals, amino radicals, and halogens,
n, m and m', which may be identical or different, are chosen from zero and 1, and
B is linked to a hetero atom of the dye radical A; and
wherein the at least one second compartment comprises a dilute solution of a chemical agent capable of rendering the at least one latent pigment insoluble.

31. The kit according to claim 30, wherein the at least one second compartment comprises a solution comprising at least one alkaline compound.

32. The kit for dyeing keratin fibers according to claim 30, wherein Y is oxygen.

33. The kit for dyeing keratin fibers according to claim 30, wherein $Z^+$ is chosen from aliphatic groups, aromatic groups, saturated and unsaturated carbocyclic groups and heterocyclic groups, and wherein $Z^+$ bears at least one quaternized nitrogen atom.

* * * * *

UNITED STATES PATENT AND TRADEMARK OFFICE
CERTIFICATE OF CORRECTION

PATENT NO. : 7,670,390 B2 Page 1 of 1
APPLICATION NO. : 12/013800
DATED : March 2, 2010
INVENTOR(S) : Alain Lagrange et al.

It is certified that error appears in the above-identified patent and that said Letters Patent is hereby corrected as shown below:

Claim 3, col. 17, line 25, "$Z^{30}$" should ready --$Z^+$--.

Signed and Sealed this

Eleventh Day of May, 2010

David J. Kappos
*Director of the United States Patent and Trademark Office*